(12) United States Patent
Farey

(10) Patent No.: US 6,203,575 B1
(45) Date of Patent: Mar. 20, 2001

(54) MODULAR SYSTEM FOR SHAFT PROSTHESES

(75) Inventor: Samuel Farey, Etupes (FR)

(73) Assignee: Sulzer Orthopaedie AG, Baar (CH)

( * ) Notice: Subject to any disclaimer, the term of this patent is extended or adjusted under 35 U.S.C. 154(b) by 0 days.

(21) Appl. No.: 09/229,135

(22) Filed: Jan. 12, 1999

(30) Foreign Application Priority Data

Jan. 16, 1998 (EP) .................................................. 98810021

(51) Int. Cl.⁷ ........................................................ A61F 2/30
(52) U.S. Cl. ........................................................ 623/18.11
(58) Field of Search ............................. 623/19.11, 19.12, 623/22.12, 25.15, 18.11, 22.16, 22.4, 22.45, 908, 911, 914; 606/89, 53, 91, 99, 102

(56) References Cited

U.S. PATENT DOCUMENTS

| | | | | |
|---|---|---|---|---|
| 3,801,989 | * | 4/1974 | McKee | 623/22.12 |
| 3,815,590 | * | 6/1974 | Deyerle | 606/98 |
| 4,003,095 | * | 1/1977 | Gristina | 623/19.12 |
| 4,404,692 | * | 9/1983 | Eftekhar | 623/23 |
| 4,642,121 | * | 2/1987 | Keller | 623/22.12 |
| 4,658,808 | * | 4/1987 | Link | 623/16.11 |
| 4,676,798 | | 6/1987 | Noiles . | |
| 4,904,269 | * | 2/1990 | Elloy et al. | 623/23.26 |
| 4,919,679 | * | 4/1990 | Averill et al. | 623/22.12 |
| 5,019,108 | * | 5/1991 | Bertin et al. | 623/23.28 |
| 5,041,141 | * | 8/1991 | Ypma et al. | 623/911 |
| 5,108,452 | * | 4/1992 | Fallin | 623/22.42 |
| 5,122,145 | | 6/1992 | Fishbane . | |
| 5,129,907 | | 7/1992 | Heldreth . | |
| 5,133,765 | * | 7/1992 | Cuilleron | 623/22.12 |
| 5,156,626 | * | 10/1992 | Broderick et al. | 623/22.12 |
| 5,312,216 | | 5/1994 | Hogg . | |
| 5,342,363 | * | 8/1994 | Richelsoph | 606/79 |
| 5,342,366 | * | 8/1994 | Whiteside et al. | 606/86 |
| 5,514,136 | * | 5/1996 | Richelsoph | 606/99 |
| 5,569,263 | * | 10/1996 | Hein | 623/23 |
| 5,593,451 | * | 1/1997 | Averill et al. | 623/23.15 |
| 5,601,567 | * | 2/1997 | Swajger et al. | 606/102 |
| 5,645,607 | | 7/1997 | Hickey . | |
| 5,720,750 | * | 2/1998 | Koller et al. | 606/85 |
| 5,741,335 | * | 4/1998 | Gerber et al. | 623/19.13 |
| 5,858,020 | * | 1/1999 | Johnson et al. | 623/23.15 |
| 5,882,295 | * | 3/1999 | McDaniel et al. | 606/89 |

FOREIGN PATENT DOCUMENTS

| | | |
|---|---|---|
| 0163121 | 12/1985 | (EP) . |
| 0373078A1 | 6/1990 | (EP) . |
| 2 727 857 | 6/1996 | (FR) . |
| WO 94/15551 | 7/1994 | (WO) . |
| WO 97/25943 | 7/1997 | (WO) . |

\* cited by examiner

*Primary Examiner*—Gene Mancene
*Assistant Examiner*—Eduardo C. Robert
(74) *Attorney, Agent, or Firm*—Townsend and Townsend and Crew LLP

(57) ABSTRACT

With the invention a modular system for the mounting of shaft prostheses is shown which have a coupling which can be fixed within a predetermined angular range between the prosthesis stem and the prosthesis head, which can be fixed by an apparatus in the prosthesis stem. Through a modular system with combinable stems and prosthesis heads of differing sizes for prostheses and test prostheses which are constructionally alike externally and in the position of the point of rotation, a variety of test prostheses and shaft prostheses arises. The test prostheses have an apparatus in the prosthesis head which permit the fixing of the head in an ideal position with a controllable function in a stem inserted in a bone. This position between the head and the stem is preserved when the test prosthesis is extracted and transferred to a mounting apparatus, in which a shaft prosthesis which is built up of analogous parts is brought into the same position and fixed.

5 Claims, 6 Drawing Sheets

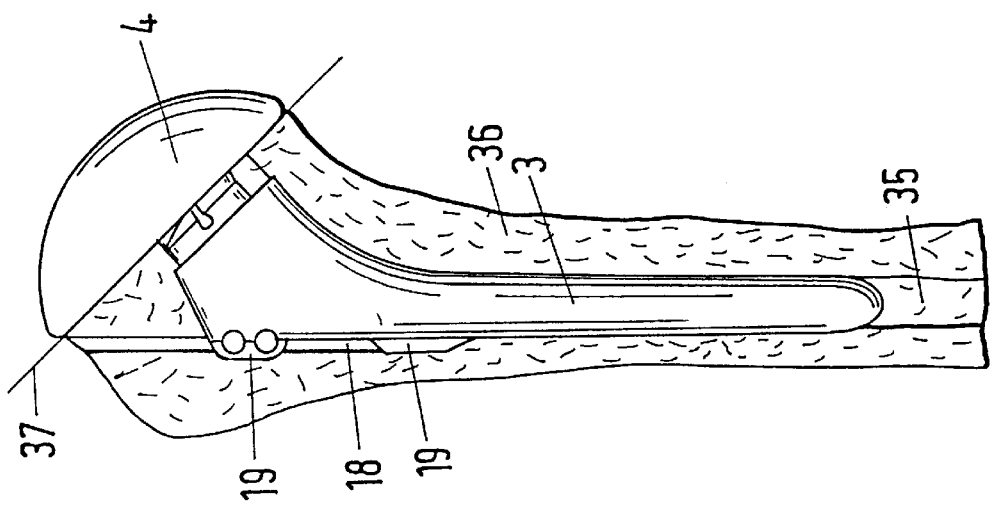
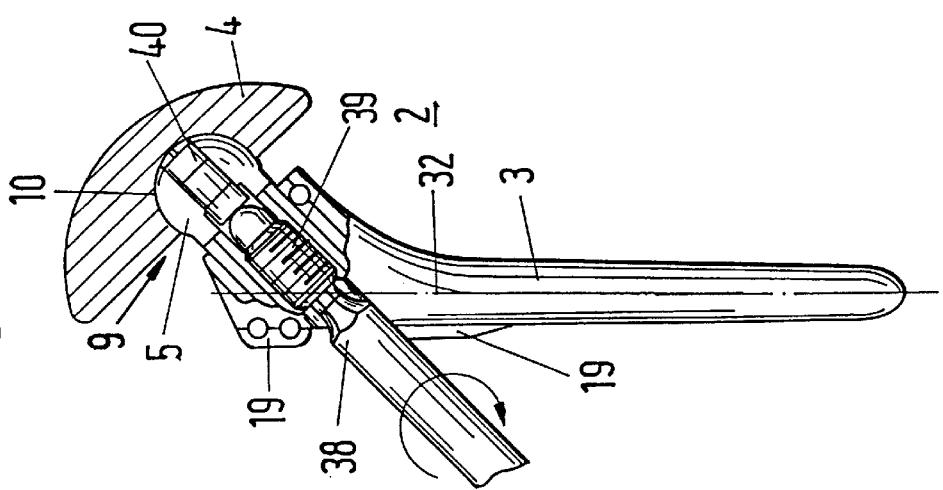
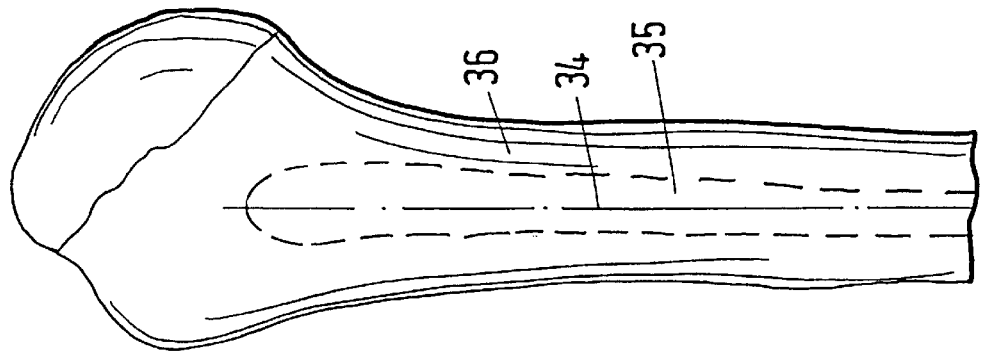

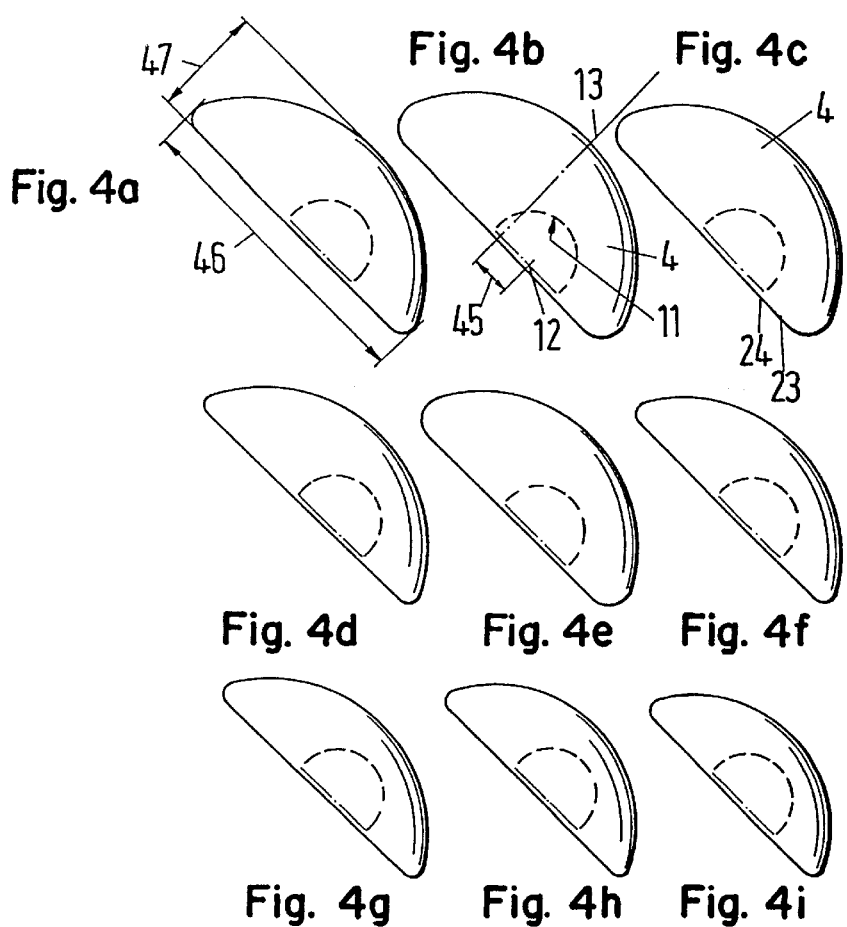
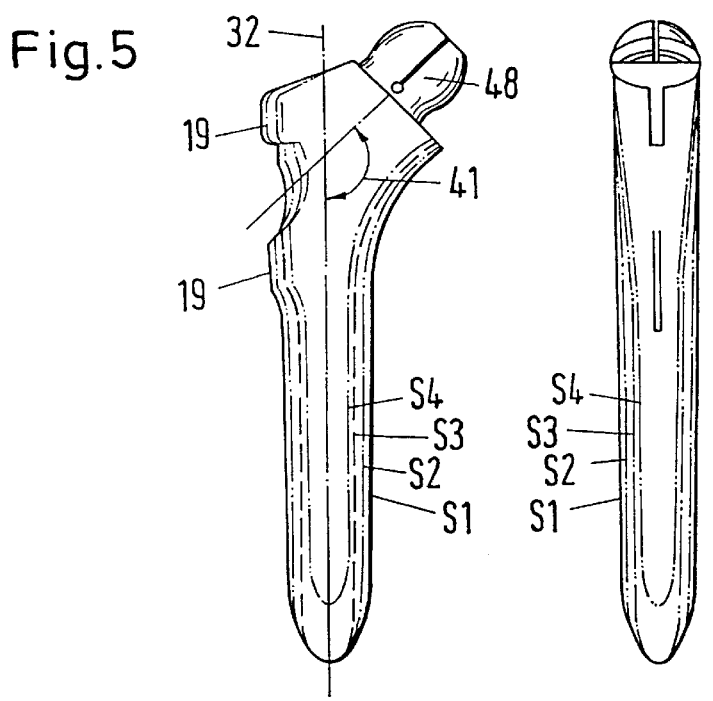

MODULAR SYSTEM FOR SHAFT PROSTHESES

BACKGROUND OF THE INVENTION

1. Field of the Invention

The present invention relates to a modular system with a mounting apparatus for the mounting of shaft prostheses.

2. Description of the Prior Art

FR-A-2 727 857 shows a shaft prosthesis for a shoulder joint which consists of a stem and a prosthesis head which are connected to one another via a fixable ball joint. The prosthesis head consists of a shallow spherical section, the underside of which is to lie on a planar resection surface of a humerus in order to completely cover off the resection surface. A spherical body which stands off from the stem in an inclined direction to the stem axis is divided up by slits into lobes which can be spread apart by a thorn which is driven into the spherical body through the stem in the inclined direction. In the prosthesis head a spherical bearing shell is worked in from the lower side which encloses the spherical body during the spreading apart and blocks it at a selectable angle to the stem axis. A disadvantage of this arrangement is that this setting of the inclination must be done in advance and that a considerable spatial imagination is required of the surgeon. Since the dimensions of the fixable ball joint must be kept small for reasons of space, a plastic deformation at the feet of the lobes is compulsory during their fixing and self inhibition is necessary in a spreading thorn for safety. This means that, with all the other advantages of this construction, the surgeon actually has only one chance in order to definitively fix the coupling.

SUMMARY OF THE INVENTION

The object of the invention is therefore to achieve a precise pre-setting of a shaft prosthesis of this kind. This is achieved by a modular system with a mounting apparatus comprising shaft prostheses which can be assembled from stems of different sizes and prosthesis heads of different sizes, with a fixable coupling existing between the stem and the prosthesis head which allows different positions and angular orientations between the prosthesis head and the stem; comprising test prostheses which can be assembled in different sizes analogously to the shaft prostheses and which have a releasably fixable coupling which can be fixed in the test prosthesis which is inserted in a bone in order to hold firmly an ideal position and angular orientation of the head of the test prosthesis with respect to its stem, which after the removal of the test prosthesis can be transmitted with the latter to the mounting apparatus in order to mutually fix a stem and prosthesis head corresponding to the test prosthesis in the mounting apparatus in the position and angular orientation of the test prosthesis.

An advantage of this arrangement consists wherein, through the modular system principle, fewer parts in the prostheses and test prostheses are required in order to cover a wide spectrum. A further advantage consists wherein the test prosthesis is movably journalled relative to the stem with its head during the insertion in order to bring the head into the most favorable position with respect to the resection surface and the articulation. The position of the head can be fixed in the state of insertion into the bone and its function tested. When the stem of the test prosthesis is inserted the head can be replaced, the new head oriented and fixed, and its function tested. The surgeon has the assurance that the shaft prosthesis which is later inserted will fulfil its function equally well.

Use of the modular system is favorable for shoulder joints, which have a comparatively low loading and therefore allow fixable ball joints as a coupling from the stem to the head. The bearing shell is arranged in the prosthesis head and has the same position relative to the lower side in spite of the different outer dimensions of the head. Through a radial displacement from the center of the bearing shell to the central axis of the head, the latter can be changed in its distance from the stem axis through rotation and can thus cover a wider spectrum of resection surfaces which are displaced differently with respect to the stem axis.

An advantageous mounting apparatus results from the fact that it has first reception apparatuses by means of which every stem size can be positioned and clamped in a unique and reproducible manner, and that it has at least one second reception apparatus which, guided, is displaceable relative to the first reception apparatuses and can be guided after a test prosthesis which is clamped in the first reception apparatus into a unique angular orientation and position of the head and fixed there in order to mutually orient and combine an equally large stem and an equally large test prosthesis in the same position and angular orientation after the removal of the test prosthesis.

A mounting apparatus of this kind can be used not only for the setting of shaft prostheses in accordance with test prostheses which have been tested in their function. They also permit, in the event of fractures of the bone which make test prostheses impossible, the setting of the shaft prostheses at a predetermined angular orientation, for example, at an intermediate angle between a coupling axis parallel to the central axis of the head and a stem axis of 130°, and a retro-torsion to the left or the right of 18°.

Instead of a floating disc which is journalled in a coupling, a fixable Cardan joint can also be used in a mounting apparatus of this kind. The second reception apparatus must basically be constituted in such a manner that it can follow the adjustment movements which are possible through the coupling.

BRIEF DESCRIPTION OF THE DRAWINGS

FIG. 1 schematically, a humerus with a joint head;

FIG. 2 shows schematically, a shaft prosthesis with a stem which can be inserted in the humerus and with a head which can be fixed thereon;

FIG. 3 shows schematically, a shaft prosthesis of FIG. 2 which is inserted in a humerus in accordance with FIG. 1;

FIG. 4 shows schematically, a side view of prosthesis heads of different sizes for a humerus prosthesis in accordance with FIG. 2;

FIG. 5 shows schematically in two views, prosthesis stems of different sizes which can be combined with prosthesis heads of FIG. 4;

DETAILED DESCRIPTION OF THE PREFERRED EXEMPLARY EMBODIMENTS

Figure 6:
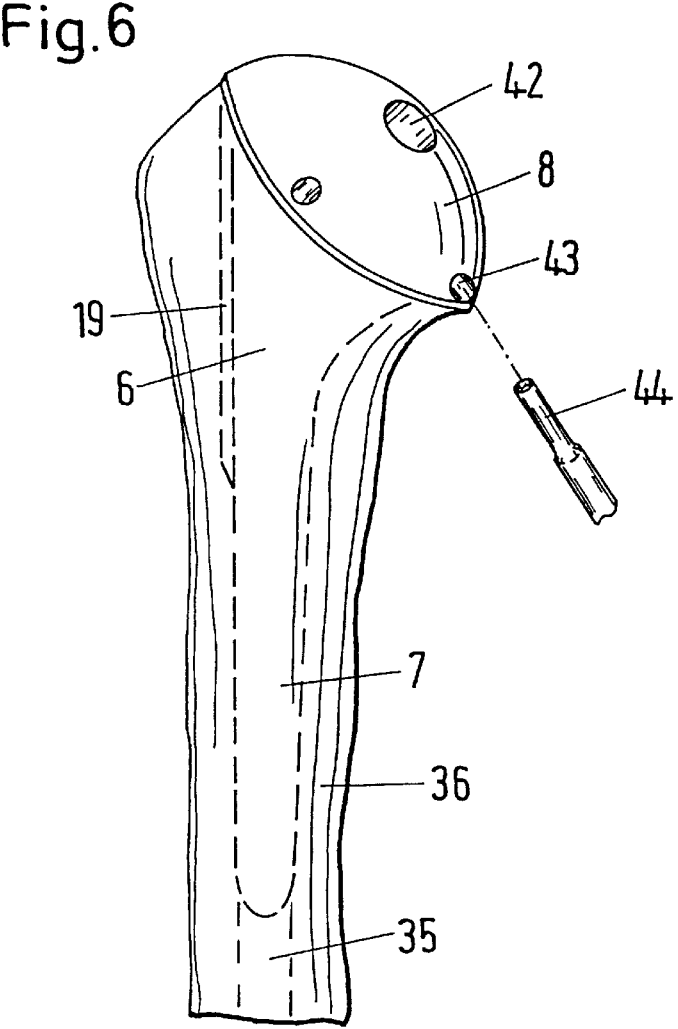
FIG. 6 shows schematically, a test prosthesis inserted in a humerus.

The figures show a modular system for the monitoring of shaft prostheses which have a coupling between the prosthesis stem 3 and the prosthesis head 4 which can be fixed in a predetermined angular range and which can be fixed through an apparatus in the prosthesis stem 3. Through a modular system with combinable stems and prosthesis heads of different sizes and prostheses 3, 4 and test prostheses which are constructionally similar outwardly and in the location of the points of rotations, a large variety of test prostheses and shaft prostheses arises. The test prostheses have an apparatus in the prosthesis head which permit the fixing of the head in an ideal position with testable function when a stem is inserted into a bone. This position between the head and the stem is preserved when extracting the test prosthesis and transferred to a mounting apparatus 1 in which a shaft prosthesis 3, 4 which is built up of analogous parts is brought into the same position and fixed.

FIGS. 1 to 5 show shaft prostheses 2 for a humerus 36 which are anchored in the extended marrow chamber 35 of the humerus. The extended marrow chamber is provided with a groove 18 which guides a fin 19 of the stem 3 and lends a unique position to the stem. The stem axis 32 and the axis 34 of the marrow chamber approximately coincide. The prosthesis shaft consists of a warm hammered alloy, for example in accordance with ISO 5832-9, and has four sizes $S_1$ to $S_4$ (FIG. 5). The stem 3 has the shape of a trumpet in order to achieve an intentional blocking during insertion. Rotational stability is achieved through the lateral fin 19 in the proximal region. A spherical head forms the coupling 5 to the prosthesis head 4. It forms an angle 41 of 130° with the stem axis 32. The spherical head is provided with a bore passing through the stem and is subdivided by elongate slits into four lobes 48 which can be bent off. A spreading apart of the lobes 48 is done by an expansion cone 40 and an expansion screw 39 which is anchored in the stem and which is turned in with a torque wrench 38 in order to limit the expansion forces. The prosthesis head 4 consists of a cast alloy (ISO 5832-4) and is executed in different diameters 46 and heights 47 (sizes a to i in FIG. 4). The lower side 23 of the head forms a planar contact surface. Each prosthesis head has the same spherical bearing shell 11, which is curved by more than 180° in longitudinal section, and has the same distance to the lower side 23 of the head. Between the center 12 of the bearing shell 11 and the central axis 13, there is a displacement 45 by means of which the prosthesis head 4 can be rotated about the center 12 of the bearing shell 11.

Figure 7:
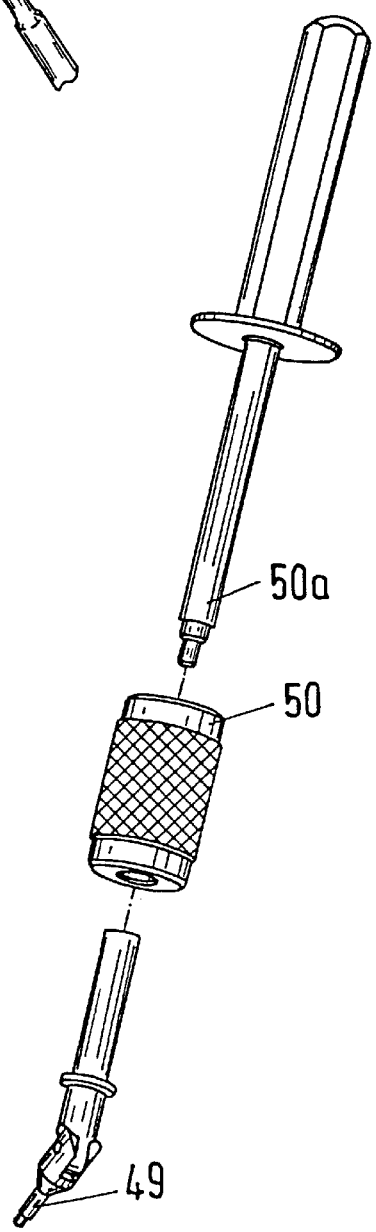
FIG. 7 shows schematically, an extraction tool for a test prosthesis in accordance with FIG. 6 with a sliding hammer which can be applied thereon.

In order that, as in FIG. 3, the prosthesis head 4 lies on a resection surface 37, covers over the latter as exactly as possible, and has a suitable height 47 for its function, test prostheses 6 which are constructionally similar in their outer dimensions are provided, of which the stems 7 and the heads 8 can be combined as in the actual shaft prostheses 2. There is likewise a coupling 9 as a fixable ball joint 10 with a similar position from the center 12 and with a similar displacement 45 with respect to the central axis in the prosthesis head 8. In contrast to the shaft prosthesis 2, the bearing of the test prosthesis 6 is rotatably held in an ideal position during the insertion by five setscrews, which can be reached with a tool 44 through bores 43 in the articulation surface in the inserted state, and can be releasably fixed after this position has been reached. An inserted test prosthesis 6 is shown in FIG. 6. At the prosthesis head 8, radially extending threaded bores 43 are provided in which setscrews are turned in which fix the bearing in the head. Five setscrews are distributed over the periphery in order that at least two of them can be reached with the tool 44 in the inserted state. A further bore 42 in the articulation surface enables access to a threading for an extraction tool 49 (FIG. 7), at which a sliding hammer 50, 50a can be applied. For a sufficiently large bearing shell 11 of the test prosthesis, the extraction tool 49 can be screwed into a threading at the spherical head of the stem 7 in order to bring the extraction forces directly onto the stem 7 and in order not to endanger the position of the fixed joint 9.

Figure 8:
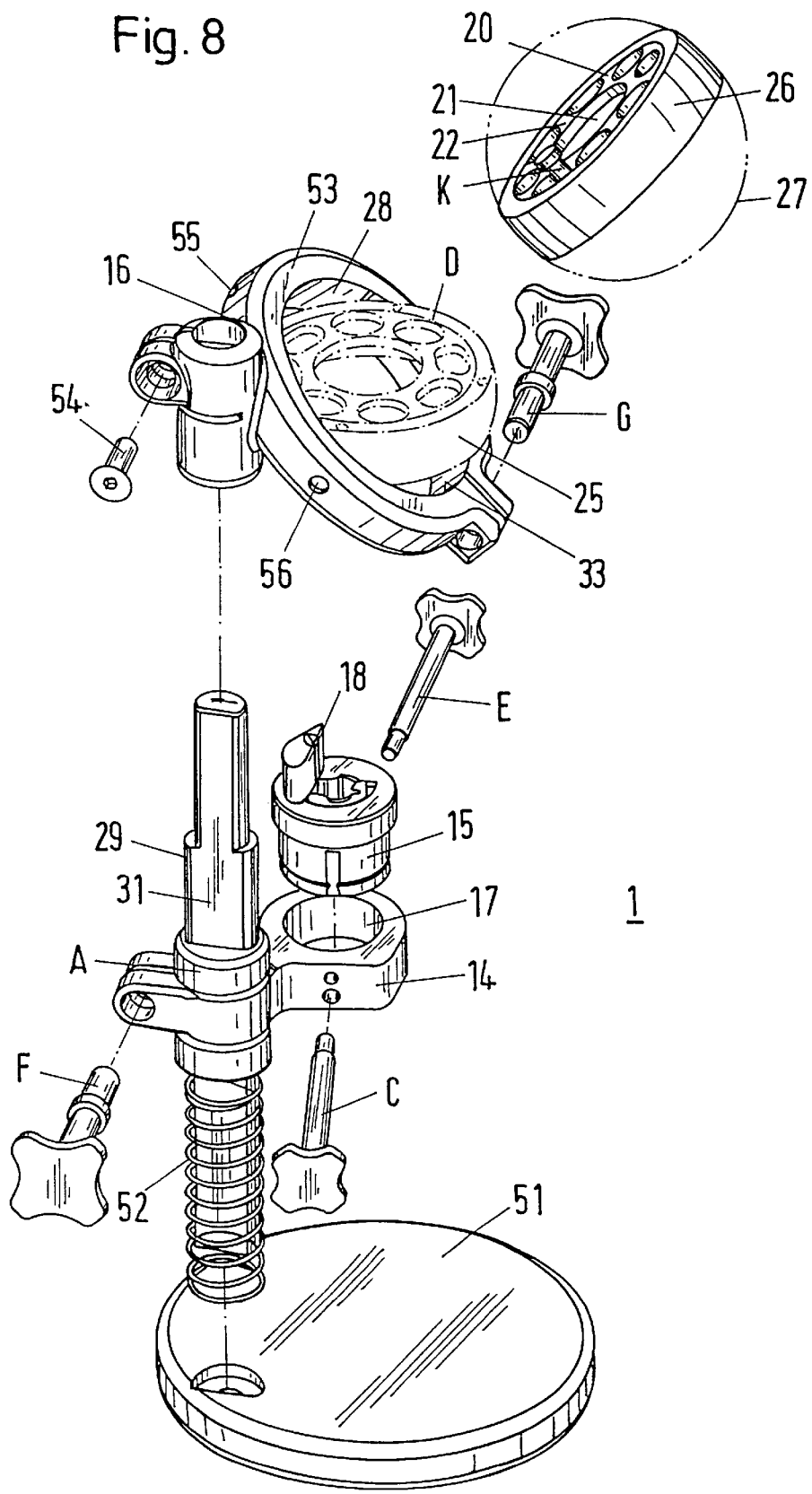
FIG. 8 shows schematically, an exploded view of a mounting apparatus for humerus prostheses.

The mounting apparatus 1 in FIG. 8 consists of a stand 29 with a foot 51. First reception apparatuses 14, 15 for prosthesis stems are connected to a sliding carriage A which can be moved at a guide 31 along the stand 29, and of which the weight can be partially compensated by means of a spring 52. The sliding carriage A can be blocked at different height positions with a screw F. Sleeves 15 which have, in each case, a reception surface and a groove 18 for a given stem size and which have the fin 19 associated therewith are secured by means of a screw C in a unique position on the sliding carriage A, 14. A screw E, by means of which an inserted stem 3, 7 can be clamped into a reproducible, unique position, engages at the sleeve 15.

A second reception apparatus 16, which is secured at the end of the stand 29 via a screw 54 carries a cut open ring 53 of which the diameter can be adjusted to a slight extent via a setting screw G. Into this ring is inserted a floating disc D (drawn in dotted lines) which is illustrated once again outside in solid lines 20. The floating disc D, 20, guided in the ring 53, can be rotated into any angular orientation desired. The outer bearing surface 26 of the floating disc 20 corresponds to the equatorial band of a spherical surface 27 for which a ring shaped counter-surface 28 has been worked into the cut open ring 53. By adjustment of the screw G, the floating disc D, 20 can be blocked at any angular orientation desired. The floating disc 20 has a central opening 21, through which prosthesis stems 3, 7 can be pushed on without contact. In addition, a rotating disc I with the mark H (FIG. 14) which can be displaced on the periphery and which can be blocked at a predetermined angular orientation with a screw K is provided on the floating disc. At the ring 53, radially insertable pins 55, 56 are provided which can position the floating disc D as abutments in a predetermined standard position which corresponds to an average position of many patients.

Figure 9:
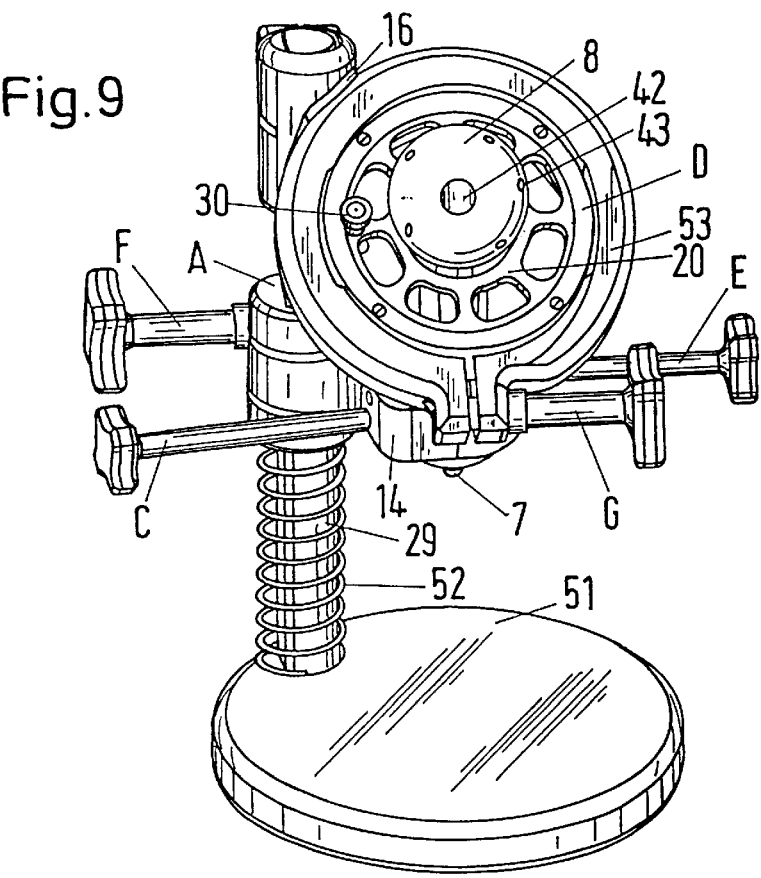
FIG. 9 shows schematically, the mounting apparatus of FIG. 8 with an inserted test prosthesis.

In FIG. 9, a test prosthesis is clamped with its stem 7 in the first reception apparatus 14 and determines with its head 8 on its lower side the angular orientation picked up at a resection surface which the floating disc D, 20 assumes during a cautions lowering of the sliding carriage A. In this position, a mark H is rotated with the screw 30, K to a marking at the head 8, which corresponds to the direction of the displacement 45, and blocks in order to store the position of the displacement for the shaft prosthesis 2 inserted later in the mounting apparatus.

Figure 10:
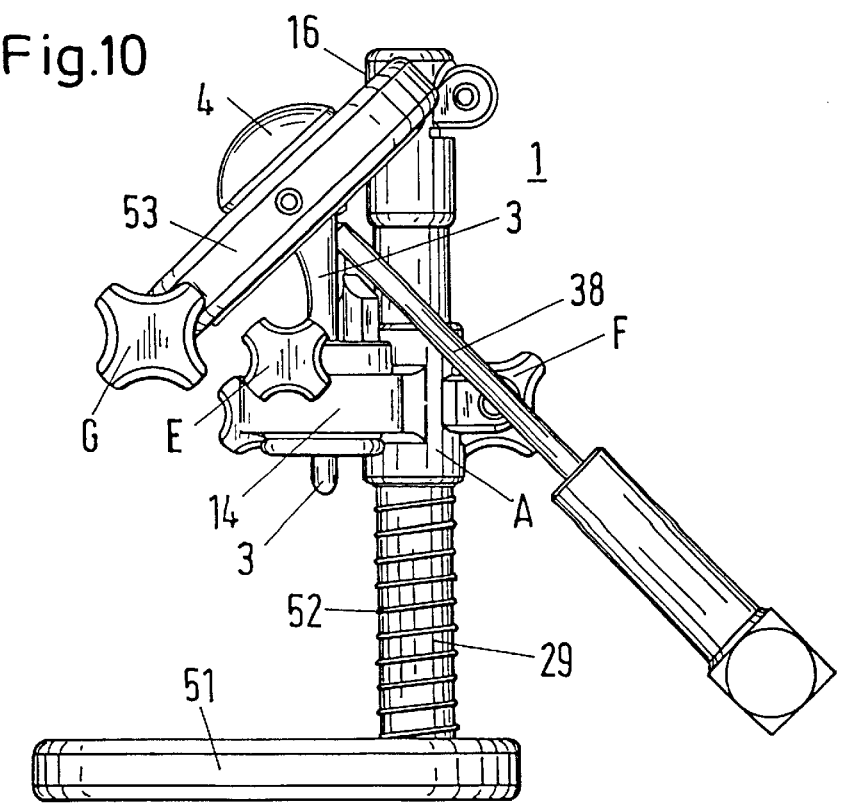
FIG. 10 shows schematically, the mounting apparatus of FIG. 8 with an inserted shaft prosthesis and with a torque wrench during the fixing of the prosthesis head.
Figure 11:
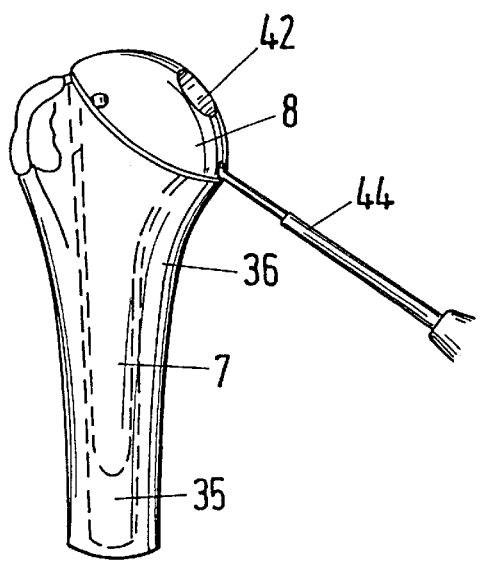
FIG. 11 shows schematically, a test prosthesis inserted in the humerus during the fixing of the prosthesis head in a preferred position relative to the prosthesis stem.

In FIG. 10 the test prosthesis has meanwhile been removed after the screw E has been released. The sliding carriage A is first brought into a somewhat higher position in order to position and to clamp the constructionally similar shaft prosthesis 2 with its stem 3 in the first reception apparatus 14. Then the sliding carriage G is cautiously lowered in order that the prosthesis head 4, which is pivotal on the stem 3, assumes the position of the blocked floating disc, i.e. the plane of the resection surface, with its lower side. At this inclination the head 4 is rotated until its marking for the displacement agrees with mark H, i.e. with the displacement of the test prosthesis. In this position the expansion screw 39 is tightened with a torque wrench 38 in order to fix the bearing 5, 11 in a controlled manner. The shaft prosthesis 2 now corresponds to the test prosthesis 6 which had previously been tested on location and can be implanted.

Figure 14:
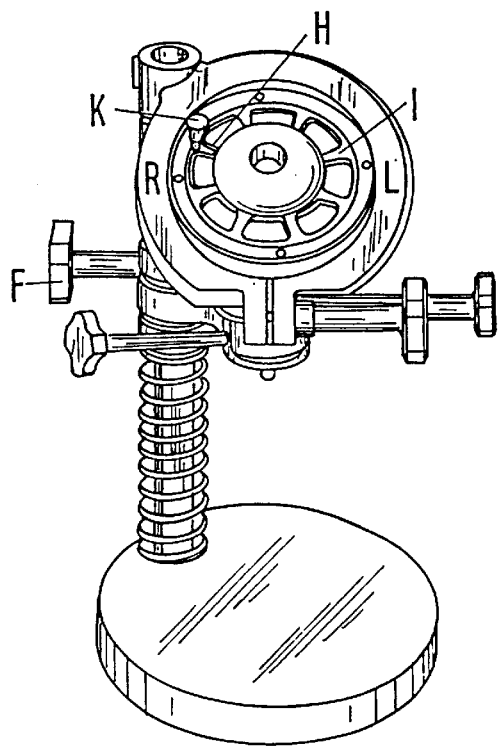
FIG. 14 shows schematically, a following moving of the display for the position of the displacement between the central axis and the bearing shell centre at the head of a test prosthesis of FIG. 13.

The steps at the test prosthesis are shown in a sequence in the FIGS. 11 to 14:

In FIG. 14 the head 8 of a suitable test prosthesis, which has been inserted with its stem 7 in a unique position in the marrow chamber 35 of a humerus, is oriented in accordance with the lay of the resection surface and is secured in this position relative to the stem 7 with the tool 44 through the turning in of setscrews. With the extraction tool 49 the shaft is gripped through a bore 42 and extracted. The remaining setscrews are likewise tightened for the improved securing of the angular orientation of the head 8.

Figure 12:
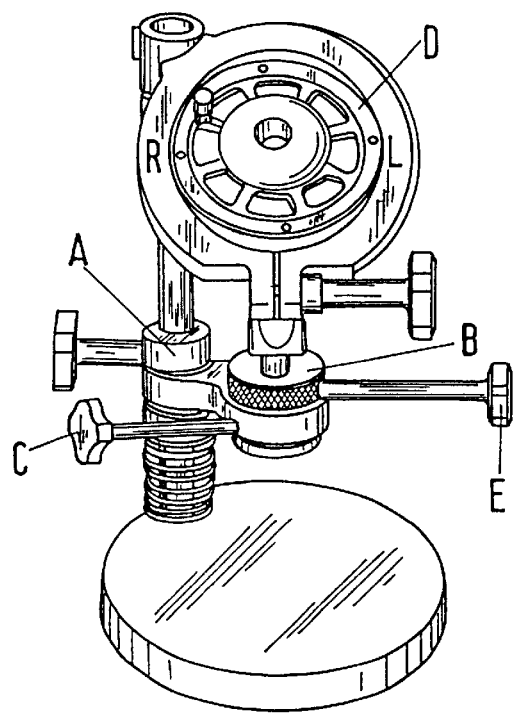
FIG. 12 shows schematically, a test prosthesis which is loosely laid into a mounting apparatus of FIG. 8 prior to the clamping in of the prosthesis stem.

In FIG. 12 the test prosthesis has been loosely placed on the floating disc D. The sliding carriage A is first moved downwardly in order to insert a sleeve B, 15 fitting with the stem 7 in the first reception apparatus and to secure it with a screw C. Then the sliding carriage A is moved upwardly and the stem 7 is positioned in the sleeve B, 15 and secured with the screw E.

Figure 13:
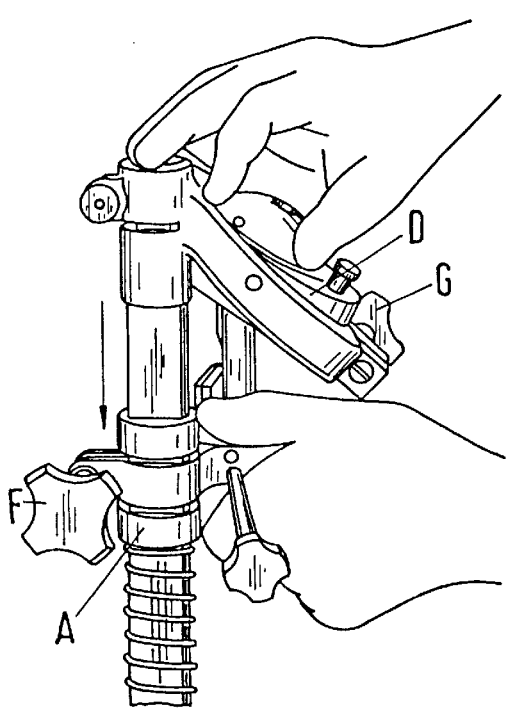
FIG. 13 shows schematically, an orientation of the inclination of a floating disc towards the lower side of the head of a test prosthesis which is clamped in at the stem.

In FIG. 13 the sliding carriage A is cautiously moved downwardly in order that the floating disc D orients itself in accordance with the inclination of the lower side of the head, and the inclination is fixed by tightening of the screw G.

In FIG. 14 a rotating disc with a mark H is pushed in the inclined plane of the floating disc D to that place which displays the position of the displacement on the head 8, and the rotating disc I is then secured with a screw K with respect to the floating disc D. The state now corresponds to the illustration of FIG. 9. The position of the test prosthesis is stored in the mounting apparatus 1 and the test prosthesis can now be removed after the release of the clamping screw E.

What is claimed is:

1. A modular system including a mounting apparatus for the mounting of shaft prostheses, the modular system comprising:

shaft prostheses that are assembled from stems of different sizes and prosthesis heads of different sizes, wherein each shaft prosthesis includes a fixable coupling between its respective stem and its respective prosthesis head, the fixable coupling allowing for different positions and angular orientations between the prosthesis head and the stem; and test prostheses that are assembled in different sizes analogously to the shaft prostheses, each test prosthesis including a releasably fixable coupling that is fixed in the test prosthesis, wherein a test prosthesis that is inserted in a bone holds an ideal position and angular orientation of a head of the test prosthesis with respect to a stem of the test prosthesis;

wherein after removal of a test prosthesis, the ideal position and angular orientation of the head of the test prosthesis with respect to the stem is transmitted with the test prosthesis to the mounting apparatus in order to mutually fix a stem and prosthesis head corresponding to the test prosthesis in the position and angular orientation in the test prosthesis in the mounting apparatus.

2. A modular system in accordance with claim 1 wherein the shaft prostheses are shoulder prostheses.

3. A modular system in accordance with claim 2 wherein the test prostheses include a coupling in the form of a fixable ball joint between the stem and the prosthesis head in the same position as the shaft prosthesis, wherein a bearing shell is arranged in the prosthesis head and a spherical body projects from the stem, wherein the bearing shell allows for capture and releasably fixing the spherical body by setscrews that are placed radially in the prosthesis head.

4. A modular system in accordance with claim 2 wherein the shoulder prostheses include a coupling in the form of a fixable ball joint between the stem and the prosthesis head, wherein a bearing shell of the ball joint is arranged in the prosthesis head.

5. A modular system in accordance with claim 4 wherein a center of the bearing shell is displaced radially with respect to a central axis defined by the prosthesis head.

* * * * *